United States Patent [19]

Barry

[11] Patent Number: 4,583,541
[45] Date of Patent: Apr. 22, 1986

[54] STERNAL STABILIZATION DEVICE

[76] Inventor: Joseph P. Barry, 5112 N. Byron Ave., Oklahoma City, Okla. 73112

[21] Appl. No.: 607,639

[22] Filed: May 7, 1984

[51] Int. Cl.⁴ .............................................. A61B 17/08
[52] U.S. Cl. .................................. 128/335; 128/92 R; 128/92 D
[58] Field of Search ................. 128/335, 92 B, 334 C, 128/336, 92 D, 92 R, 92 G

[56] References Cited

U.S. PATENT DOCUMENTS

| 3,695,271 | 10/1972 | Chodorow | 128/335 |
| 3,831,608 | 8/1974 | Kletschka et al. | 128/335 |
| 3,983,878 | 10/1976 | Kawchitch | 128/335 |
| 4,364,382 | 12/1982 | Mennen | 128/92 D |
| 4,503,848 | 3/1985 | Caspar et al. | 128/92 D |
| 4,512,346 | 4/1985 | Lemole | 128/335 |

FOREIGN PATENT DOCUMENTS 215065 5/1961 Austria ............................... 128/335

Primary Examiner—Robert Peshock
Assistant Examiner—Cary E. Stone
Attorney, Agent, or Firm—Robert K. Rhea

[57] ABSTRACT

In a sternal closure device an elongated substantially strap-like member provided with a flat back surface flatly overlies the anterior surface of a severed sternum. The forward surface of the member is convex and longitudinally grooved for nesting the tied or twisted end portions of suture wires extending across the posterior of the sternum and projecting forwardly through cooperating pairs of holes formed in the member on opposing sides of the groove.

3 Claims, 2 Drawing Figures

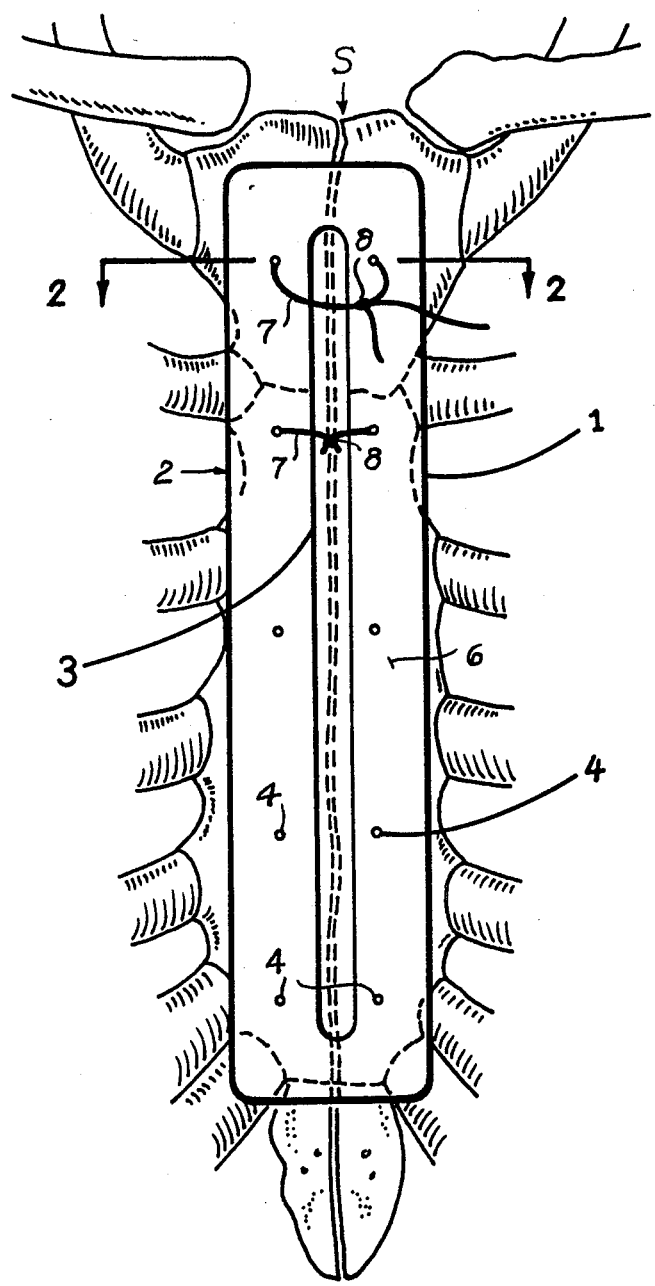
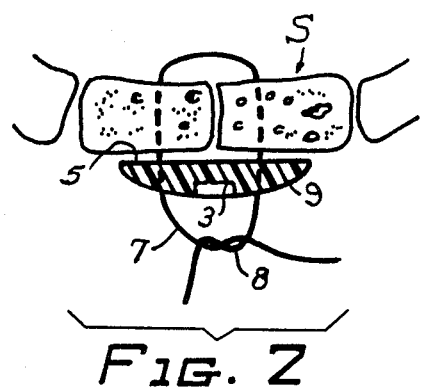
Fig. 1
Fig. 2

STERNAL STABILIZATION DEVICE

BACKGROUND OF THE INVENTION
1. Field of the Invention

The present invention relates to surgical devices and more particularly to a splint type device for joining the severed sections of a divided sternum following chest surgery.

This invention is important in that it has such widespread applications for the field of chest and heart surgery. The present method of obtaining access to the heart and great vessels is via a median sternotomy which is an incision made through the skin and the sternum (breast bone). The sternum is actually sawed in two and then it is spread apart so that the surgeons can operate on the heart to do their various procedures, i.e., coronary artery bypasses, heart valve replacements, corrective surgery for the various congenital heart defects. Once the operations are completed then the surgeons have to close the sternum securely. The current method of doing this is to pass a piece of stainless steel wire around and under the sternum and twist these wires into a knot. These knots are then bent over so as hopefully not to stick into the patients flesh as this can cause pain and infections due to the physical injury to the surrounding tissues. My invention is designed primarily to enable the surgeons to close the sternum more securely and efficiently, hopefully with fewer problems than are presently being encountered. There are many articles throughout the medical literature today dealing with the complications seen after median sternotomies. These range from wires. breaking, wires protruding through the skin, separation of the sternum, failure of the sternum to heal, infections and loose or unstable sternums. In addition to these physical problems we must consider the emotional aspects the patients have to deal with when faced with additional surgical procedures, a longer hospital stay, prolonged courses of antibiotics, to say nothing of the significant financial burdens that the patients and families have to assume.

The magnitude of this enormous problem encountered when dealing with these patients is easily seen if one realizes that there are approximately 150,000 of these procedures being performed annually throughout the world. With my invention, the surgeon will place the wires around the sternum and then bring the ends of the wires up through holes made in the device, twist the wires and place the knots in the groove where they will be recessed and then covered with a medical adhesive to seal them in. Hopefully this procedure will allow the surgeons to tie the sternum together more securely thereby allowing for a more stable sternum with fewer wire breakages, fewer wires protruding through the skin and fewer infections. In addition, this added stability will allow the patients to breathe more deeply since the pain from the edges of the sternum rubbing together should be minimized and thereby prevent some of the pneumonias that are seen in patients who do not breathe deeply enough after surgery because of pain from their incisions. Finally, since this device will be covered with a soft rubber material it should feel more comfortable against the sternum and where it comes in contact with the patients skin over the chest. Infections will also be minimized since the tissues in contact with the device will not be damaged by any sharp wires.

My sternal stabilization device is a much needed apparatus in todays surgical armamentarium. It is applicable for use in every operation that utilizes a median sternotomy approach. I sincerely feel that the routine use of this device makes it possible for the countless number of patients who are undergoing heart surgery to have a much safer and less painful recovery period. We must remember that when complications occur that this delays the entire rehabilitation period and inflicts more emotional and financial burdens upon the patients, their families and the entire health care delivery system.

2. Description of the Prior Art

| U.S. PAT. NO. | PATENTEE | ISSUE DATE |
| --- | --- | --- |
| 4,119,092 | GIL | 10/10/78 |
| 4,297,993 | HARLE | 11/03/81 |

Gil discloses a method of reducing bone fractures, especially fractures of the long bones of the upper and lower extremities.

Harle discloses an aid for osteosynthesis for inner fixation of fractures.

Neither of these two inventions are applicable for fractures of the sternum because it is not a long bone and does not have the internal area capable of allowing an internal device to be installed in it. Harle's disclosure was also to be used as a vehicle with which to introduce antibiotics into the fracture site.

SUMMARY
Summary of the Invention

An elongated generally strap-like member, formed from rigid material, having a planar back surface is adapted to substantially contiguously overlie, in transverse and longitudinal relation, the anterior surface of a longitudinally divided sternum of a patient. The member is characterized by a forward or front transversely convex surface merging with the perimeter of the flat back surface. The convex surface is provided with a central longitudinally extending indentation or groove of sufficient depth and width to receive knotted or twisted end portions of suture wires when disposed therein. The member is provided with a plurality of pairs of holes extending through its front and back surface arranged to define a pair of rows of holes disposed on respective longitudinal sides of the groove with the holes forming the respective pairs arranged in opposition transversely of the member. The member is preferably covered with a layer of resilient inert material. A plurality of wires, one for each pair of holes, extend transversely of the severed sternum posterior surface and project forwardly through the holes with the end portions of the respective wire tied or twisted together to hold the severed edges of the sternum in juxtaposition and the twisted wire ends are disposed within the groove.

The principal objects of this invention are to provide a surgical device to contiguously overlie a patient's servered sternum for securing the sternum thereto and preventing movement of one portion of the sternum relative to the other portion and prevent twisted suture wire ends protruding toward and into the flesh or skin overlying the sternum.

BRIEF DESCRIPTION OF THE DRAWINGS

FIG. 1 is a front elevation view, illustrating the device in place on a fragmentary section of the sternum which is shown with the rib attachments; and, FIG. 2 is a horizontal cross section along the lines 2—2 of FIG. 2.

DESCRIPTION OF THE PREFERRED EMBODIMENT

Like characters of reference designate like parts in those figures of the drawings in which they occur.

In the drawings:

The reference numeral 1 indicates the device, as a whole, including an elongate member 2 which is rectangular strap-like in general configuration, preferably formed from rigid plastic material, and having a length and width cooperatively overlying the sternum S of a patient with which the device is to be used following major surgery requiring longitudinal division of the patient's sternum. One longitudinal surface of the member forms a back surface 5 which is substantially planar and overlies the anterior surface of the patient's sternum. The opposite or forward surface 6 of the member is convex merging at its respective lateral limits with the back planar surface to form a relatively thin perimeter for the member. The convex forward surface 6 is provided with a longitudinally extending recess or groove 3 terminating at its respective ends in spaced relation with respect to the ends of the member. The depth of the groove is less than its width but sufficient to nest the tied or twisted end portions of suture wires, as presently explained.

The member 2 is further provided with a plurality of pairs of holes 4 respectively arranged on opposing sides of the groove and extend through the front and back surfaces of the member defining a pair of rows of holes on respective sides of the groove.

A relatively thin layer of resilient material, such as the rubber-like material presently marketed under the trademark Silastic, indicated by the heavy line 9 (FIG. 2), surrounds the entire member.

OPERATION

In use the member 2 is placed on the severed sternum S as described hereinabove and a plurality of stainless steel wires 7, one for each pair of holes, is extended intermediate its ends across the posterior of the sternum with the respective end portions of each wire brought forwardly and projected through the respective pair of the pairs of holes 4. The juxtaposed end portions of each wire 7 are then twisted or tied together, as at 8, after drawing the severed sections of the sternum together in a manner well known by those skilled in the art, before twisting or tying the wires. The respective end portions of each wire, extending beyond the knot or twist 8, is cut off and the knots are forced flatly into the groove 3. A length of medical adhesive, not shown, is then applied to the front surface of the member to overlie the groove 3 and the knots 8 therein.

Obviously the invention is susceptible to changes or alterations without defeating its practicability. Therefore, I do not wish to be confined to the preferred embodiment shown in the drawings and described herein.

I claim:

1. A stabilizer for holding a severed sternum closed, comprising:
    an elongated rigid generally strap-like member having a generally flat back surface for longitudinally overlying the anterior surface of a severed sternum in transverse spanning relation,
    said member having a forward surface and having a recess therein intermediate its length and substantially medially its width,
    said member having longitudinally and transversely spaced-apart pairs of holes respectively extending through its front and back surfaces on opposing sides of the recess; and,
    a plurality of wires each to be extended intermediate its ends transversely across the sternum posterior and project at its respective end portions through a respective pair of said pairs of holes for tying or twisting the respective wire end portions together adjacent the front surface of said member.

2. The stabilizer according to claim 1 in which the front surface of said member is transversely convex and merges with
    the perimeter of the back surface to define a relatively thin edge when compared with the thickness of the member medially its width.

3. The stabilizer according to claim 1 and further including:
    a layer of Silastic rubber surrounding said member.

* * * * *